United States Patent [19]

Frei et al.

[11] Patent Number: 4,904,814

[45] Date of Patent: Feb. 27, 1990

[54] PROCESS FOR THE PREPARATION OF TERT-ALKYL ESTERS

[75] Inventors: Urs Frei, Liebistorf; Rudolf Kirchmayr, Marly, both of Switzerland

[73] Assignee: Ciba-Geigy Corporation, Ardsley, N.Y.

[21] Appl. No.: 153,375

[22] Filed: Feb. 8, 1988

[30] Foreign Application Priority Data

Feb. 13, 1987 [CH] Switzerland .................. 534/87

[51] Int. Cl.$^4$ .................. C07C 67/03; C07C 120/00; C07D 239/02; C07D 215/14; C07D 233/66; C07D 311/02

[52] U.S. Cl. .................. 560/204; 544/335; 546/174; 546/326; 548/217; 548/224; 548/343; 549/287; 549/345; 558/416; 560/20; 560/64; 560/65; 560/96; 560/190

[58] Field of Search .......... 560/20, 64, 65, 96, 560/204, 190; 558/416; 544/335; 546/174, 326; 548/217, 224, 343; 549/287, 345

[56] References Cited

U.S. PATENT DOCUMENTS 4,730,080 3/1988 Drent .................. 560/204

OTHER PUBLICATIONS

D. S. Wulfman et al, Synthesis, 1972, pp. 49.

*Primary Examiner*—Werren B. Lone

*Assistant Examiner*—Vera C. Clarke

*Attorney, Agent, or Firm*—Stephen V. O'Brien

[57] ABSTRACT

Process for the preparation of tert-alkyl esters of the formula I

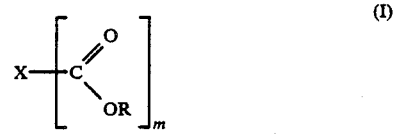

in which m is 1 or 2, R is $C_4$–$C_{12}$tert-alkyl and X, if m=1, is unsubstituted or halogen-substituted alkyl, cycloalkyl, unsubstituted or substituted aryl or aralkyl, or an aromatic heterocyclic radical and, if m=2, is a direct bond, $(CH_2)_n$, in which n can be an integer from 1 to 8, or 1,2-, 1,3- or 1,4-phenylene, by reaction of an ester of the formula II

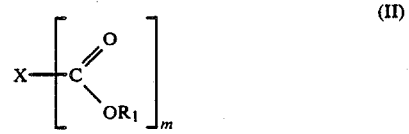

in which $R_1$ is methyl or ethyl, with an alcohol ROH in the presence of a catalyst customary for transesterifications.

7 Claims, No Drawings

PROCESS FOR THE PREPARATION OF TERT-ALKYL ESTERS

The present invention relates to a process for the preparation of tert-alkyl esters by catalytic transesterification of methyl or ethyl esters with tert-alkyl alcohols.

No catalytic transesterifications of primary lower alkyl esters with tertiary alcohols to give tertiary esters, analogously to the generally known methods for the preparation of longer-chain primary and secondary alkyl esters, are known. The reason for this is that the skilled in the art has expected only poor yields because of the steric hindrance.

In Synthesis 1972, 49, D. S. Wulfman et al. describe a partial transesterification of 7,7-dimethoxycarbonylnorcarane to give 7-exo-tert-butoxycarbonyl-7-endo-methoxycarbonylnorcarane by reaction with potassium t-butylate in a molar ratio of 1:1 in t-butyl alcohol in the presence of molecular sieves. This method is not generally applicable and in particular cannot be used for industrial preparation of tertiary esters since certain carboxylic acid esters undergo undesirable side reactions in the presence of such large amounts of bases (1:1 mol). The unavoidable removal of the interfering by-products thus formed consumes time, labour and energy.

It has now been found, surprisingly, that tert-alkyl esters can be obtained in excellent yields and without the formation of troublesome by-products by reaction of methyl or ethyl esters with tert-alkyl alcohols in the presence of catalytic amounts of the catalysts customary for transesterifications with primary and secondary alcohols.

The present invention accordingly relates to a process for the preparation of tert-alkyl esters of the formula I

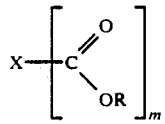

in which m is 1 or 2, R is $C_4$–$C_{12}$tert-alkyl and X, if m=1, is unsubstituted or halogen-substituted alkyl, cycloalkyl, unsubstituted or substituted aryl or aralkyl, or an aromatic heterocyclic radical and, if m=2, is a direct bond, $-(CH_2)_n-$, in which n can be an integer from 1 to 8, or 1,2-, 1,3- or 1,4-phenylene, by reaction of an ester of the formula II

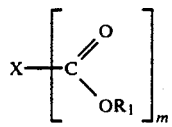

in which m and X are as defined above and $R_1$ is methyl or ethyl, with $m \times 2$ to $m \times 10$ mol of an alcohol of the formula ROH, in which R is as defined above, in the presence of catalytic amounts of a catalyst chosen from the group consisting of dibutyltin oxide, lithium amide, aluminium tert-butylate, potassium tert-butylate, sodium, lithium, potassium, sodium methylate, sodium ethylate and titanium alcoholates, the methanol or ethanol formed being simultaneously distilled off.

$C_4$–$C_{12}$tert-Alkyl R is, for example, tert-butyl, tert-pentyl, 1-methyl-1-ethyl-propyl, 1,1-diethyl-propyl, 1,1-dimethyl-butyl, 1-methyl-1-ethyl-butyl, 1-diethyl-butyl, 1-ethyl-1-propyl-butyl, 1,1-dipropyl-butyl, 1,1,3-trimethyl-butyl, 1,1-dimethyl-pentyl, 1-methyl-1-ethyl-pentyl, 1,1-diethyl-pentyl, 1-methyl-1-propyl-pentyl, 1-ethyl-1-propyl-pentyl, 1,1-dipropyl-pentyl, 1-ethyl-1-butyl-pentyl, 1,1,3-trimethyl-pentyl, 1,1-dimethyl-4-ethyl-pentyl, 1,1-dimethyl-3-ethyl-pentyl, 1,1-dimethyl-hexyl, 1,1-diethyl-hexyl, 1,1-dipropyl-hexyl, 1,1-dimethyl-heptyl, 1,1-diethyl-heptyl, 1,1-dimethyl-octyl, 1,1-diethyl-octyl and 1,1-dimethyl-decyl. tert-Butyl and, in particular, tert-pentyl are preferred.

Alkyl X is advantageously $C_4$–$C_{18}$alkyl, for example n-butyl, sec-butyl, tert-butyl, n-pentyl, tert-pentyl, n-hexyl, 2-ethyl-hexyl, n-octyl, decyl, dodecyl, hexadecyl or octadecyl.

Halogen-substituted alkyl X is, for example, an alkyl group as defined above substituted by one or more chorine or bromine atoms.

Cycloalkyl X is advantageously $C_5$–$C_7$cycloalkyl, for example cyclopentyl, cycloheptyl and, in particular, cyclohexyl.

Ary X is, for example, phenyl or naphthyl, and substituted aryl X is, for example, phenyl which is substituted by one or two chlorine, bromine, $C_1$–$C_4$alkyl (for example methyl, ethyl, propyl, isopropyl, n-butyl, sec-butyl or tert-butyl), $C_1$–$C_4$alkoxy (for example methoxy, ethoxy, propoxy, isopropoxy, n-butoxy, sec-butoxy or tert-butoxy), cyano or nitro radicals.

Aralkyl X is, for example, unsubstituted or $C_1$–$C_4$alkyl-substituted benzyl or phenethyl.

An aromatic heterocyclic radical X is advantageously a mono-, di- or tricyclic radical. This can be purely heterocyclic or can contain a heterocyclic ring and one or more fused-on benzene rings, for example pyridyl, pyrimidyl, pyrazinyl, triazinyl, furyl, pyrrolyl, thienyl, quinolyl, cumarinyl, benzofuranyl, benzimidazolyl, benzoxazolyl, dibenzofuranyl, benzothienyl, dibenzothienyl, indolyl, carbazolyl, pyrazolyl, imidazolyl, oxazolyl, isoxazolyl, thiazolyl, indazolyl, benzothiazolyl, pyridazinyl, cinnolinyl, quinazolinyl, quinoxalinyl, phthalazinyl, phthalazindionyl, phthalimidyl, chromonly, naphtholacetamyl, quinolonyl, maleimidyl, naphthyridinyl, benzimidazolonyl, benzoxazolonyl, benzothiazolonyl, benzothiazothionyl, quinazolonyl, quinoxalonyl, phthalazonyl, dioxopyrimidinyl, pyridonyl, isoquinolonyl, isoquinolinyl, isothiazolyl, benzisoxazolyl, benzisothiazolyl, indazolonyl, acridinyl, acridonyl, quinazolinedionyl, quinoxalinedionyl, benzoxazinedionyl, benzoxazinonyl and naphthalimidyl. Pyridyl, pyrimidyl, pyrazinyl, triazinyl, furyl, pyrrolyl, thienyl, quinolyl, cumarinyl, benzofuranyl, benzimidazolyl and benzoxazolyl are preferred.

An ester of the formula II in which $R_1$ is methyl is preferably used as the starting substance.

Preferred catalysts are lithium amide, sodium and, in particular, lithium.

The process according to the invention is of particular interest for the preparation of tert-alkyl esters of the formula I from an ester of the formula II and an alcohol of the formula ROH in which R is $C_4$–$C_8$tert-alkyl and X, if m=1, is $C_4$–$C_8$alkyl or phenyl which is unsubstituted or substituted by chlorine, methyl, ethyl, methoxy, ethoxy, cyano or nitro and, if m=2, a direct bond, $-(CH_2)_n-$, in which n is an integer from 1 to 8, or 1,3- or 1,4-phenylene.

The process according to the invention is particularly preferred for the preparation of tert-alkyl esters of the formula I from an ester of the formula II and an alcohol of the formula ROH in which m is 2, R is tert-butyl or tert-pentyl and X is ethylene.

The ester of the formula II is advantageously mixed with the required amount of tert-alcohol of the formula ROH at room temperature. For esters of the formula II in which m is 1, 200–1,000, preferably 300–600 mol % of tert-alcohol, and for esters of the formula II in which m is 2, 400–2,000, preferably 800–1,200 mol % of tert-alcohol, based on the ester of the formula II are used. The catalyst is then added in amounts of 8–30, preferably 10–15 mol %, based on the ester of the formula II. The reaction mixture is refluxed, the primary alcohol of the formula $R_1OH$ formed, partly mixed with tert-alcohol of the formula ROH, being distilled off over a fractionating column. Vigreux columns and in particular packed columns are especially suitable for this purpose. The amount of alcohol mixture distilled off is advantageously replaced with new tert-alcohol every three hours. The desired tert-alkyl esters are obtained in excellent yields after 8–16, preferably 9–12 hours in the case of the monoesters and after 16–30, preferably 20–26 hours in the case of the diesters.

The esters of the formula II and the alcohols of the formula ROH are known substances. Where individual representatives of these substances are novel, they can be prepared by generally known processes.

The following examples illustrate the invention without limiting it.

EXAMPLE 1

146 g of dimethyl succinate (1 mol) are taken in 1 liter of absolute tert-amyl alcohol (11 mol) at room temperature. 0.7 g of lithium (0.1 mol) are then added. The reaction mixture is boiled under reflux at about 100° C. and the methanol formed, partly mixed with tert-amyl alcohol, is continuously distilled off over a fractionating column (packed column) at 86°–87° C. The amount of alcohol mixture distilled off is supplemented by new tert-alcohol every three hours (about 350 ml in total). After 22 hours, the alcohol is distilled off completely and the oily residue is washed with water/cyclohexane to remove the lithium salt. The organic phase is separated off, evaporated and distilled in vacuo (65° C. under 10 Pa). 200 g of pure di-tert-pentyl succinate are obtained.

| Analysis for $C_{14}H_{26}O_4$ | | |
|---|---|---|
| | C | H |
| Calculated | 65.09 | 10.14 |
| Found | 64.9 | 10.1 |

EXAMPLES 2–22

The procedure followed is as in Example 1, starting from 1 mol of ester of the formula

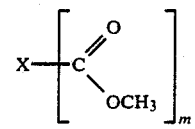

and a tert-alcohol ROH, in the presence of 0.1 mol of catalyst, the meaning of m, R and X, the catalyst, the amount of tert-alcohol and the reaction time being given in the following table. The corresponding tert-esters of the formula I are obtained.

| Example | X | m | R | Amount of tert-alcohol | Catalyst | Reaction time in hours |
|---|---|---|---|---|---|---|
| 2 | (phenylene) | 1 | tert-Pentyl | 5 mol | Lithium | 10 |
| 3 | (pyridyl) | 1 | tert-Pentyl | 5 mol | Lithium | 10 |
| 4 | (furyl) | 1 | tert-Pentyl | 5 mol | Lithium | 10 |
| 5 | $CH_3$―$(CH_2)_3$― | 1 | tert-Pentyl | 5 mol | Lithium | 10 |
| 6 | $CH_3$―(phenylene) | 1 | tert-Pentyl | 5 mol | Lithium | 10 |
| 7 | $CH_3$―$(CH_2)_{10}$― | 1 | tert-Pentyl | 5 mol | Lithium | 10 |
| 8 | $CH_3$―$(CH_2)_{16}$― | 1 | tert-Pentyl | 5 mol | Lithium | 10 |

-continued

| Example | X | m | R | Amount of tert-alcohol | Catalyst | Reaction time in hours |
|---|---|---|---|---|---|---|
| 9 | BrCH$_2$— | 1 | tert-Pentyl | 5 mol | Lithium | 10 |
| 10 | 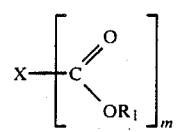 | 1 | 1,1-Dimethylpentyl | 5 mol | Lithium | 10 |
| 11 | Direct bond | 2 | tert-Pentyl | 11 mol | Lithium | 22 |
| 12 | —CH$_2$—CH$_2$— | 2 | tert-Pentyl | 11 mol | Dibutyltin oxide | 22 |
| 13 | —CH$_2$—CH$_2$— | 2 | tert-Pentyl | 11 mol | LiNH$_2$ | 22 |
| 14 | —CH$_2$—CH$_2$— | 2 | tert-Pentyl | 11 mol | Al tert-butylate | 22 |
| 15 | —CH$_2$—CH$_2$— | 2 | tert-Pentyl | 11 mol | K tert-butylate | 22 |
| 16 | —CH$_2$—CH$_2$— | 2 | tert-Pentyl | 11 mol | Sodium | 22 |
| 17 | 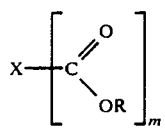 | 2 | tert-Pentyl | 11 mol | Lithium | 22 |
| 18 | | 2 | tert-Pentyl | 11 mol | Lithium | 22 |
| 19 | —CH$_2$— | 2 | tert-Pentyl | 11 mol | Lithium | 22 |
| 20 | ─(CH$_2$)$_3$─ | 2 | tert-Pentyl | 11 mol | Lithium | 22 |
| 21 | ─(CH$_2$)$_8$─ | 2 | tert-Pentyl | 11 mol | Lithium | 22 |
| 22 | —CH$_2$CH$_2$— | 2 | tert-Butyl | 11 mol | Lithium | 22 |

EXAMPLE 23

The procedure followed is as in Example 1, with the sole exception that diethyl succinate is used as the starting substance. Di-tert-pentyl succinate is obtained in an equally good yield and purity as in Example 1.

What is claimed is:

1. A process for the preparation of a tert-alkyl ester of the formula I $$X\!\!-\!\!\left[\!\!C\!\!\begin{array}{c}\diagup\!\!O\\ \diagdown\!\!OR\end{array}\!\!\right]_m \quad (I)$$

in which m is 1 or 2, R is C$_4$–C$_{12}$tert-alkyl and X, when m=1, is unsubstituted or halogen-substituted alkyl, cycloalkyl, unsubstituted or substituted aryl or aralkyl, or an aromatic heterocyclic radical and, when m=2, is a direct bond, ─(CH$_2$)$_n$─, in which n can be an integer from 1 to 8, or 1,2-, 1,3- or 1,4-phenylene, by reaction of an ester of the formula II $$X\!\!-\!\!\left[\!\!C\!\!\begin{array}{c}\diagup\!\!O\\ \diagdown\!\!OR_1\end{array}\!\!\right]_m \quad (II)$$

in which m and X are as defined above and R$_1$ is methyl or ethyl, with m×2 to m×10 mol of an alcohol of the formula ROH, in which R is as defined above, in the presence of catalytic amounts of a catalyst chosen from the group consisting of dibutyltin oxide, lithium amide, aluminium tert-butylate, potassium tert-butylate, sodium, lithium, potassium, sodium methylate, sodium ethylate and titanium alcoholates, the methanol or ethanol formed being simultaneously distilled off.

2. The process according to claim 1, wherein X in the formulae I and II, where m=1, is C$_4$–C$_{18}$alkyl, C$_4$–C$_{18}$alkyl which is substituted by chlorine or bromine, C$_5$–C$_7$cycloalkyl, phenyl which is unsubstituted or substituted by chlorine, bromine, C$_1$–C$_4$alkyl, C$_1$–C$_4$alkoxy, cyano or nitro, naphthyl, or benzyl or phenethyl which is unsubstituted or substituted by C$_1$–C$_4$alkyl, or pyridyl, pyrimidyl, pyrazinyl, triazinyl, furyl, pyrrolyl, thienyl, quinolyl, cumarinyl, benzofuranyl, benzimidazolyl or benzoxazolyl.

3. The process according to claim 1, wherein an ester of the formula II and an alcohol of the formula ROH in which R is $C_4$–$C_8$tert-alkyl and X, when m=1, is $C_4$–$C_8$alkyl or phenyl which is unsubstituted or substituted by chlorine, methyl, ethyl, methoxy, ethoxy, cyano or nitro and, when m=2, a direct bond, $-(CH_2)_n-$, in which n is an integer from 1 to 8, or 1,3- or 1,4-phenylene, are used as the starting substances.

4. The process according to claim 1, wherein an ester of the formula II in which $R_1$ is methyl is used as the starting substance.

5. The process according to claim 1, wherein an ester of the formula II and an alcohol of the formula ROH in which m is 2, R is tert-butyl or tert-pentyl and X is ethylene are used as the starting substances.

6. The process according to claim 1, wherein the catalyst is used in an amount of 8–30 mol %, based on the ester of the formula II.

7. The process according to claim 1, wherein lithium, lithium amide or sodium is used as the catalyst.

* * * * *